United States Patent
Liu et al.

[11] Patent Number: 6,134,946
[45] Date of Patent: Oct. 24, 2000

[54] NANO-CRYSTALLINE POROUS TIN OXIDE FILM FOR CARBON MONOXIDE SENSING

[75] Inventors: Chung-Chiun Liu, Cleveland Heights; Robert F. Savinell, Solon; Zhihong Jin, Cleveland, all of Ohio

[73] Assignee: Case Western Reserve University, Cleveland, Ohio

[21] Appl. No.: 09/069,136

[22] Filed: Apr. 29, 1998

[51] Int. Cl.$^7$ ............................. G01N 27/00; G01N 27/12
[52] U.S. Cl. ............................................................ 73/31.06
[58] Field of Search ................................ 73/31.05, 31.06

[56] References Cited

U.S. PATENT DOCUMENTS 5,942,676   8/1999   Potthast et al. .......................... 73/31.06

FOREIGN PATENT DOCUMENTS

| | | | |
|---|---|---|---|
| 59-26041 | 2/1984 | Japan | 73/31.06 |
| 3-59450 | 3/1991 | Japan | 73/31.06 |
| 6-174674 | 6/1994 | Japan | 73/31.06 |

OTHER PUBLICATIONS

Vogel et al., "Quantum–sized PbS, CdS, $Ag_2S$, $Sb_2S_3$, and $Bi_2S_3$ Particles as Sensitizers for Various Nanoporous Wide–Bandgap Semiconductors," J. Phys. Chem., vol. 98, pp. 3183–3188 (1994).

Mulvaney et al., "Electron Transfer in Aqueous Colloidal $SnO_2$ Solutions," Langmuir, vol. 6, pp. 567–571 (1990).

Wilson et al., "Sol–Gel Materials for Gas Sensing Applications," Sensors and Actuators B., 18–19 pp. 506–510 (1994).

Takahata, "Tin Oxide Sensors, Development and Applications," in Chemical Sensor Technology, vol. 1, pp. 39–55, (Seiyama, Ed. 1988).

Dieéguez et al., "Morphological analysis of nanocrystalline $SnO_2$ for gas sensor applications," Sensors and Actuators B 31 (1996) pp. 1–8.

Fliegel et al., "Preparation, development if microstructure, electrical and gas–sensitive properties of pure and doped $SnO_2$ powders," Sensors and Actuators B, 18–19 (1994) pp. 474–477.

*Primary Examiner*—Daniel S. Larkin
*Attorney, Agent, or Firm*—Fay, Sharpe, Fagan, Minnich & McKee, LLP

[57] ABSTRACT

A tin oxide sol is deposited on platinum electrodes (12) of a sensor (10). The sol is calcined at a temperature of 500 to 800° C. to produce a thin film of tin oxide with a thickness of about 150 nm to 2 $\mu$ and having a nano-crystalline structure with good stability. The sensor rapidly detects reducing gases, such as carbon monoxide, or hydrocarbons and organic vapors. Sensors using films calcined at around 700° C. have high carbon monoxide selectivity with a response time of around 4 minutes and a recovery time of 1 minute, and therefore provide good detection systems for detection of trace amounts of pollutants such as toxic and flammable gases in homes, industrial settings, and hospitals.

24 Claims, 2 Drawing Sheets

NANO-CRYSTALLINE POROUS TIN OXIDE FILM FOR CARBON MONOXIDE SENSING

This invention was made with government support under Grant No. NAG3-1741 awarded by NASA. The government has certain rights in this invention.

BACKGROUND OF THE INVENTION

The present invention relates to the gaseous detection arts. It finds particular application in conjunction with metal oxide sensors for detection of carbon monoxide, and will be described with particular reference thereto. It should be appreciated, however, that the invention is also applicable to the detection of other gaseous reducing chemicals, such as hydrogen, hydrogen sulfide, hydrocarbons, and organic vapors, including toluene.

The quality of indoor air affects the health and well-being of building occupants. Concerns over the control and improvement of indoor air quality have lead to the development of a number of gaseous sensors capable of detecting toxic and pollutant gases, such as carbon monoxide, carbon dioxide, hydrogen sulfide, chlorine, nitrogen oxides, ammonia, and sulfur dioxide, as well as combustible gases, such as hydrogen, methane, and other flammable organic vapors.

Metal oxide-based sensors using oxides of zinc, tin, titanium, and other semiconductive oxides have been evaluated for their abilities to detect specific gases. Tin oxide-based sensors have shown particular promise as they exhibit a high sensitivity to certain gases at relatively low operating temperatures. Such sensors detect gases by exhibiting a measurable change in the resistance of the bulk oxide when a gas or chemical vapor is adsorbed onto the surface of the oxide.

The sensitivity of a sensor is influenced by the microstructure of the sensing surface. Surface area to volume ratio, grain size, and pore size of the metal oxide particles which comprise the surface are understood to affect the performance of the sensor.

Thin film sensors are desirable because of their relatively small size and low power consumption. Such sensors may be prepared in a number of ways, including sputtering, physical vapor deposition, and chemical vapor deposition. Sputtering and physical vapor deposition techniques produce relatively thin films, of the order of a few hundred nanometers or less. Although such films exhibit good sensitivity to gases to be detected, they often have poor stability due to their low mechanical strength. Sensors produced by chemical vapor deposition tend to suffer from poor film uniformity as the film often shows an "island" texture.

Recently, sol-gel technology has been developed for the preparation of tin oxide powders. Two sol-gel synthesis routes are known. One route involves hydrolysis of tin alkoxide to the oxide and is discussed by Wilson, et al. ("Sol-Gel Materials for Gas Sensing Applications", Sensors and Actuators B., 18–19 pp. 506–510 (1994)) and Takahata ("Tin oxide Sensors, Development and Applications," in Chemical Sensor Technology, Vol 1, pp. 39–55 (Seiyama, Ed. 1988)). Another route employs hydrolysis of tin (IV) chloride, as disclosed by Vogel, et al. ("Quantum-sized PbS, CDs, $Ag_2S$, $Sb_2S_3$, and $Bi_2S_3$ Particles as Sensitizers for Various Nanoporous Wide-Bandgap Semiconductors", J. Phys. Chem., Vol. 98, pp. 3183–3188 (1994), and Mulvaney, et al. ("Electron Transfer in Aqueous Colloid $SnO_2$ Solutions," Langmuir, Vol. 6, pp. 567–571 (1990)).

The present invention provides a new tin oxide sensor, having improved long-term stability and reproduceability, for rapid detection of carbon monoxide and other pollutant gases, which overcomes the above referenced problems and others.

SUMMARY OF THE INVENTION

In accordance with one aspect of the present invention, a sensor for rapid detection of reducing gases, hydrocarbons, or organic vapors is provided. The sensor includes a substrate which supports a plurality of electrodes, a film which includes monodisperse tin oxide having a structure with a high surface to volume ratio, and a heater which heats the sensor to a selected operating temperature. The sensor has improved long-term stability and reproduceability.

In accordance with another aspect of the present invention, a method of preparing a semiconducting film for a sensor for detection of reducing gases, hydrocarbons, and organic vapors is provided. The method includes forming a sol which includes tin oxide and depositing the sol on electrodes of the sensor. The method further includes calcining the sol to produce a film having particles which consist of tin oxide. Optionally, a dopant is included in the film for increasing the selectivity of the sensor to a specific pollutant.

In accordance with yet another aspect of the present invention, a method for the detection of reducing gases, pollutants, hydrocarbons, and organic vapors is provided. The method includes forming a sol which includes tin oxide and depositing the sol on electrodes of a sensor. the method further includes calcining the sol to produce a film having nano-crystalline particles which consist of tin oxide and exposing the sensor to a gaseous mixture containing a reducing gas, pollutant, hydrocarbon, or organic vapor to be detected. Further, the method includes detecting a change in an electrical property of the sensor which corresponds to a measure of a concentration of the reducing gas, pollutant, hydrocarbon, or organic vapor to be detected, in the mixture.

One advantage of the present invention is that it enables low concentrations of carbon monoxide to be rapidly detected.

Another advantage of the present invention is that it provides a stable nano-structural tin oxide sensing surface having an extended useful life.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
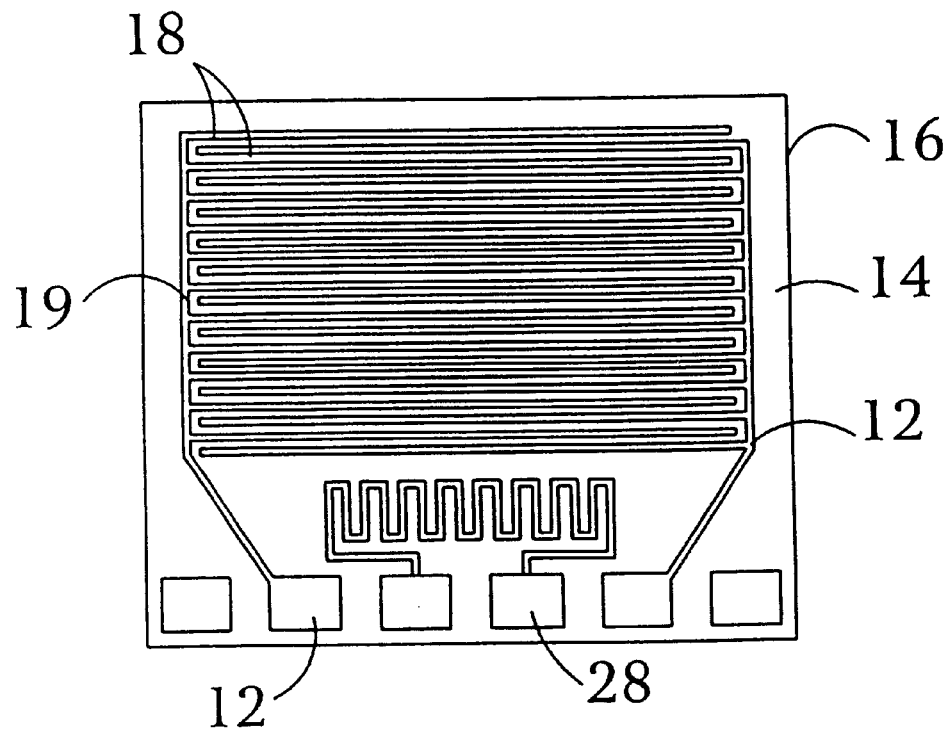
FIG. 1 is a front view of a preferred embodiment of a tin oxide sensor for detection of carbon monoxide and other gaseous and vapor pollutants in accordance with the present invention.
Figure 2:
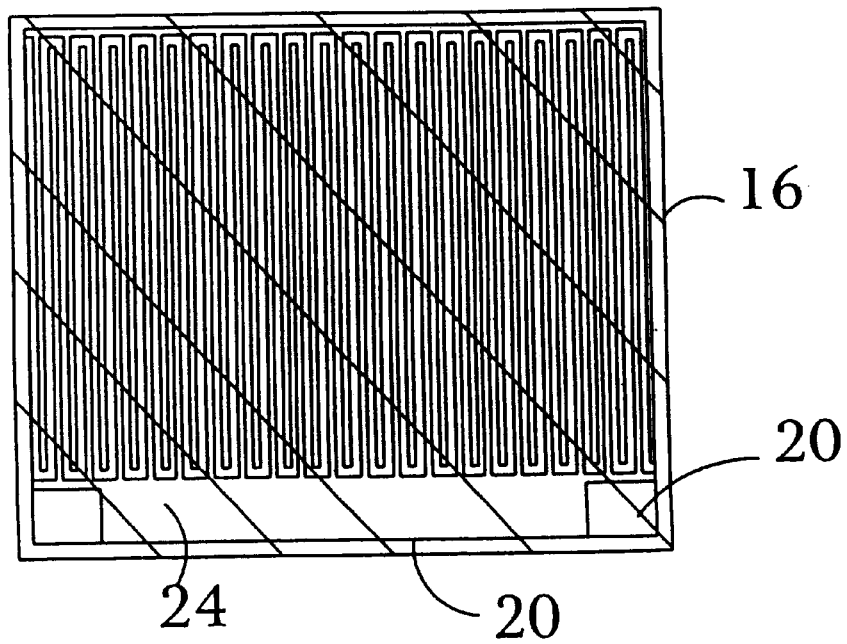
FIG. 2 is a rear view of the tin oxide sensor of FIG. 1.
Figure 3:
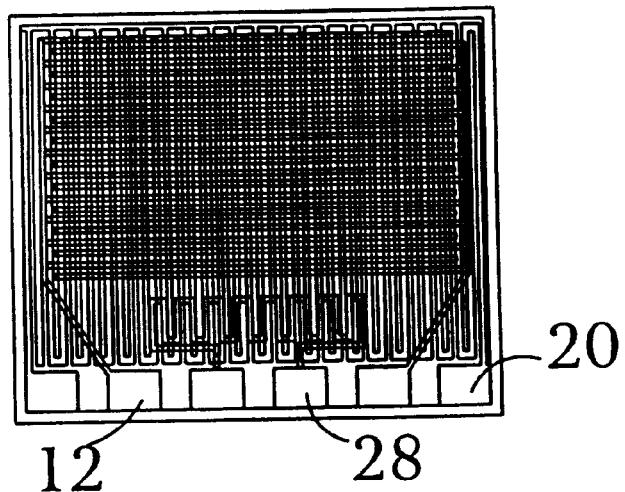
FIG. 3 illustrates a sectional view of the tin oxide sensor of FIGS. 1 and 2; and, FIG. 4 is a schematic diagram of a system for detecting carbon monoxide and other gaseous and vapor pollutants according to the present invention.

With reference to FIGS. 1, 2, and 3, a tin oxide sensor 10 for the detection of carbon monoxide and other reducing gases, hydrocarbons and organic vapors includes electrodes 12, laid down on a front face 14 of a substrate 16. The electrodes 12 are preferably formed from platinum, although other electrically conductive materials, such as gold or carbon, are also contemplated. The substrate may be formed from any suitable inert supporting material, such as alumina, silicon, glass, or plastic. An alumina substrate with a thickness of about 0.65 mm provides a suitable support for the electrodes. The electrodes include pairs of closely-spaced interdigitated elements 18, preferably laid down by photolithographic reduction and thick film silk-screen metallization printing. On a substrate 16 with a front face 14 having dimensions of about 15 mm×13 mm, electrodes having about four pairs of interdigitated sensing elements 18 are conveniently deposited. The platinum electrodes are coated with a thin film of tin oxide. A heater, such as a meander platinum resistance heater 20, is printed on a rear face 22 of the substrate 16. A thick dielectric layer 24 of material, such as glass, insulates the heater.

Figure 4:
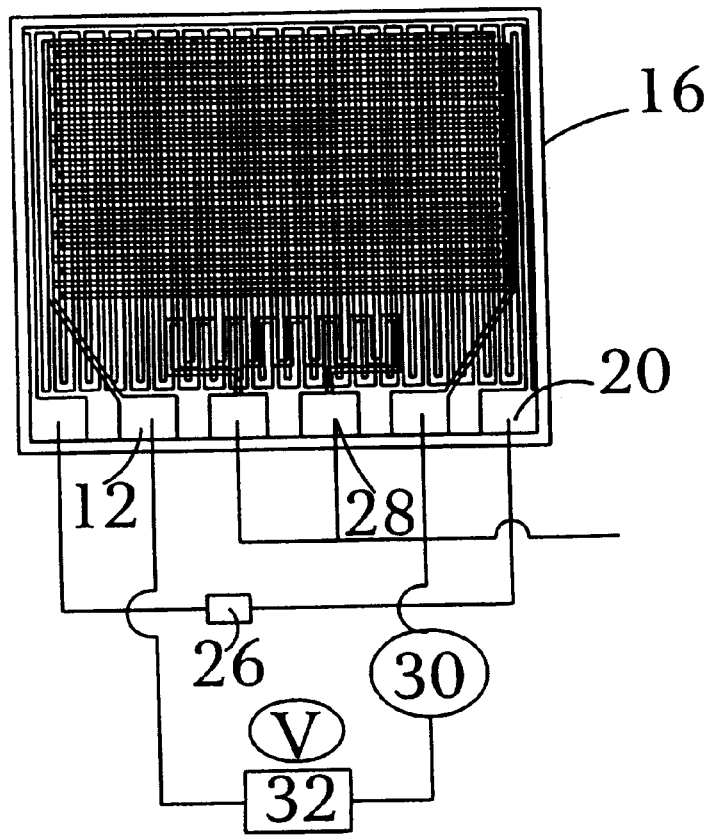

With reference also to FIG. 4, the heater is preferably controlled by a constant voltage power supply 26. The wattage applied by the power supply provides a selected operating temperature for the sensor. A temperature detector, such as a K type thermocouple 28, in thermal contact with the rear of the sensor, monitors the operating temperature of the sensor. The conductance of the tin oxide film varies with operating temperature. The heater heats the film to an operating temperature which optimizes conductance, typically in the range of from about 200° C. to about 400°C. Optionally, for gases which must be decomposed on the oxide surface prior to detection, the heater heats the sensor to a sufficient temperature for decomposing the gas.

In operation, a constant DC voltage (negative with respect to the ground) is applied to the platinum electrodes. An inverting operational amplifier 30 converts current flowing in the sensor to a voltage output. A combination of suitable data acquisition software and electrochemical equipment 32 controls data acquisition and performs AC impedance measurements. Alternatively, monitoring equipment known in the art of sensor manufacture, detects changes in resistance of the tin oxide film or detects another electrically measurable property of the sensor, which changes as the concentration of the pollutant gas changes.

The ability of an oxide film to detect a particular pollutant gas is generally expressed in terms of gas sensitivity. Gas sensitivity, S is defined as the ratio of the sensor conductance in an air and pollutant gas (such as carbon monoxide) mixture, $G_S$, to the sensor conductance in pure dry air, $G_O$.

$$S=G_S/G_O$$

While particular reference is made herein to the detection of carbon monoxide, use of the sensor to detect other gases is also contemplated. For ease of reference, however, the sensor will be described with particular attention to detection of carbon monoxide, with the understanding that other reducing gases, such as hydrogen, hydrogen sulfide, hydrocarbons, and organic vapors are similarly detected.

To prepare the tin oxide film, a stable, aqueous colloidal tin oxide sol is prepared by a method similar to that of Mulvaney, et al. ("Electron Transfer in Aqueous Colloid $SnO_2$ Solutions", Langmuir, Vol. 6, pp. 567–571 (1990)), which is incorporated herein by reference. Tin chloride is first hydrolyzed with a dilute ammonium hydroxide, under ice cooling, in a nitrogen atmosphere. The resulting tin oxide gel precipitate is washed with water to remove traces of chloride ion.

The tin oxide sol is obtained by peptizing the tin oxide gel precipitate with ammonia solution and then refluxing the resultant solution for several hours until the solution becomes viscous. The concentration of the tin oxide in the sol gel formed in this manner is about 4–5% of sol by weight. Optionally, a binder is added to the sol. The sol gel contains highly monodisperse tin oxide particles of around 3 nanometers in diameter.

To coat the platinum electrodes with the Titanium oxide sol, spin coating is preferably used. Suitable spin coating conditions are 3000 rpm for 4 minutes. Alternatively, other methods of coating conventionally known in the art are employed.

After laying a thin coating of the gel sol on the electrodes 12, the film is dried in air at 100° C. for about 30 min and then calcined in air for about 30 min in an oven at a 15° C./min heating rate. The calcination temperature influences the size of the tin oxide particles in the film formed on the electrodes. Above about 800° C., the particle size increases and the sensitivity of the sensor decreases. A preferred calcination temperature is from about 500° C. to about 800° C., with a particularly preferred calcination temperature of 500–700°°C. In this temperature range, the tin oxide particles have a nano-structure, i.e. a particle diameter of below 100 nm, and preferably around 10 nanometers or less, and showed good film integrity. Sensors having tin oxide films calcined at about 700° C. have a response time of around four minutes and a subsequent recovery time of about 1 minute, or less.

The choice of film thickness is a compromise between the operating life of the sensor and the response time. For a sensor with a relatively fast response time, the thickness of the tin oxide film is preferably about 150nm–$2\mu$, although thinner or thicker films may be used. Films of this thickness prepared by the method described show good film integrity and stability, despite being generally thinner than oxide films generated by conventional methods.

The sensor is capable of measuring low concentrations of carbon monoxide or other reducing gases. For laboratory or household use, the sensor preferably detects carbon monoxide concentrations in the range of 0 to about 100 ppm, more preferably in the range of 10 to 100 ppm.

Catalytic dopants, such as palladium, platinum, or metal oxides, such as copper oxide, are optionally used in combination with the tin oxide film to enhance the selectivity of the sensor to particular gases, as is conventionally known in the art. The dopant may be addded to at least an upper surface of the film, which increases sensitivity of the sensor to a specific gas vapor. Palladium and platinum, in particular, improve the sensitivity of the sensor to carbon monoxide. The dopant may include copper oxide for the specific detection of hydrogen sulfide gas. These may be added in a number of ways, such as mixing the dopant with the sol or directly coating the dopant on the tin oxide film in the form of a liquid salt or as particles of the selected metal.

EXAMPLE

Sensors coated with thin films of tin oxide were prepared according to the method described herein, and calcined at various temperatures. TABLE 1 shows typical particle size and pore size distributions for tin oxide films calcined at temperatures between 500 and 800° C. and the respective sensitivities to 63 ppm carbon monoxide at an operating temperature of 350° C.

TABLE 1

| | Calcination Temperature | | | |
|---|---|---|---|---|
| | 500° C. | 600° C. | 700° C. | 800° C. |
| Particle Size and standard deviation | 7 ± 1.9 nm | 8 ± 1.7 nm | 10 ± 2.5 nm | 15 ± 4.1 nm |
| Pore size and standard deviation | 5 ± 1.6 nm | 5 ± 1.5 nm | 6 ± 1.7 nm | 9 ± 3.8 nm |
| Sensitivity to CO (S) | 2.7 | 3.3 | 7.7 | 2.6 |

As can be seen from TABLE 1, pore size and particle size increase with the calcination temperature. At a 350° C. operating temperature, the tin oxide film calcined at 700° C. had the highest sensitivity to carbon monoxide. This level of sensitivity is much higher than that reported for tin oxide films prepared by conventional methods. For films calcined at temperatures between 500° C. and 700° C. the conductance of the film increases at a selected operating temperature. Above 700° C. the conductance decreases.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A sensor for rapid detection of pollutant gases and vapors, the sensor comprising:
    a substrate which supports a plurality of electrodes;
    a heater which heats the sensor to a selected operating temperature; and
    a film on the electrodes which includes tin oxide, the film having a structure with a high surface to volume ratio, the film being formed by a method which includes:
        forming a sol which includes tin oxide;
        depositing the sol on the electrodes of the sensor; and
        calcining the sol on the electrodes at a temperature of about 700° C.

2. A sensor for rapid detection of reducing gases, hydrocarbons, or organic vapors, the sensor comprising:
    a substrate which supports a plurality of electrodes;
    a film which includes monodisperse tin oxide having a structure with a high surface to volume ratio, the film being formed by depositing a sol containing tin oxide over surfaces of the electrodes and calcining the sol on the electrodes at a temperature of from about 600° C. to about 700° C; and
    a heater which heats the sensor to a selected operating temperature.

3. The sensor of claim 2, wherein the substrate is selected from the group consisting of alumina, silicon, plastic, and glass.

4. The sensor of claim 3, wherein the substrate is alumina.

5. The sensor of claim 2, wherein the electrodes include a pair of platinum interdigitated electrodes.

6. The sensor of claim 2, wherein the film has a thickness of from about 150 nanometers to about 2 $\mu$.

7. The sensor of claim 2, wherein the film includes tin oxide particles having an average diameter of about 7–15 nanometers.

8. The sensor of claim 2, wherein the film includes tin oxide particles having an average pore size of from about 5–9 nanometers.

9. The sensor of claim 8, wherein the film includes tin oxide particles having an average pore size of from about 5–6 nanometers.

10. The sensor of claim 2, wherein the sensor exhibits a sensitivity to a reducing gas of from about 2.6 to about 7.7 expressed in terms of a ratio of sensor conductance in an air and reducing gas mixture to sensor conductance in pure dry air at an operating temperature of about 350° C.

11. The sensor of claim 2, wherein the sensor detects a concentration of a reducing gas of 100 ppm or less in about four minutes, or less.

12. The sensor of claim 11, wherein the reducing gas is carbon monoxide.

13. The sensor of claim 2, wherein the film includes a binder.

14. The sensor of claim 2, wherein the film includes a dopant which improves a sensitivity of the sensor to a specific gas.

15. The sensor of claim 14, wherein the dopant includes one of the group comprising palladium, platinum, and copper oxide.

16. The sensor of claim 15, wherein the dopant includes one of palladium and platinum and wherein the specific gas is carbon monoxide.

17. The sensor of claim 14, wherein the dopant includes copper oxide and wherein the specific gas is hydrogen sulfide.

18. A sensor for rapid detection of reducing gases, hydrocarbons, or organic vapors, the sensor comprising:
    a substrate which supports a plurality of electrodes;
    a film which includes monodisperse tin oxide having a structure with a high surface to volume ratio, the film being formed by depositing a sol containing tin oxide over surfaces of the electrodes and calcining the electrodes at a temperature of at least 500° C., such that the film includes tin oxide particles having an average diameter of about 7–10 nanometers; and
    a heater which heats the sensor to a selected operating temperature.

19. A method of preparing a semiconducting film for a sensor for detection of reducing gases, hydrocarbons, and organic vapors, the method comprising:
    forming a sol which includes tin oxide;
    depositing the sol on electrodes of the sensor; and
    calcining the sol at a temperature of about 700° C. to produce a film having particles which include tin oxide.

20. The method of claim 19, wherein the step of forming a sol includes:
    hydrolyzing tin chloride to form a tin oxide gel;
    peptizing the tin oxide gel with an ammonia solution; and
    refluxing the peptized tin oxide gel until a viscous sol is formed.

21. The method of claim 19, wherein the step of depositing the sol on the electrodes includes:
    spin coating the electrodes with the sol.

22. The method of claim 19, further including:
    adding a dopant to at least an upper surface of the film which increases sensitivity of the sensor to a specific gas or vapor.

23. A method for the detection of reducing gases, pollutants, hydrocarbons, and organic vapors, the method comprising:
    forming a sol which includes tin oxide;
    depositing the sol on electrodes of a sensor;
    calcining the sol at a temperature of from about 600° C. to about 700° C. to produce a film having nanocrystalline particles which include tin oxide;

exposing the sensor to a gaseous mixture containing a reducing gas, pollutant, hydrocarbon, or organic vapor to be detected; and detecting a change in an electrical property of the sensor which corresponds to a measure of a concentration of the reducing gas, pollutant, hydrocarbon, or organic vapor to be detected, in the mixture.

24. The method of claim 23, wherein the reducing gas is carbon monoxide, the concentration of carbon monoxide in the mixture is about 100 ppm or less and wherein the step of detecting the change in the electrical property of the sensor includes detecting the change in about four minutes or less.

* * * * *